US012138349B2

(12) United States Patent
Vangsgaard et al.

(10) Patent No.: US 12,138,349 B2
(45) Date of Patent: Nov. 12, 2024

(54) PROCESS FOR SPRAY DRYING A GLP-1 PEPTIDE

(71) Applicant: Novo Nordisk A/S, Bagsvaerd (DK)

(72) Inventors: Ole Vangsgaard, Vaerloese (DK); Marlene Hoerslev Hansen, Ballerup (DK)

(73) Assignee: Novo Nordisk A/S, Bagsvaerd (DK)

( * ) Notice: Subject to any disclaimer, the term of this patent is extended or adjusted under 35 U.S.C. 154(b) by 557 days.

(21) Appl. No.: 17/438,969

(22) PCT Filed: Mar. 13, 2020

(86) PCT No.: PCT/EP2020/056744
§ 371 (c)(1),
(2) Date: Sep. 14, 2021

(87) PCT Pub. No.: WO2020/187712
PCT Pub. Date: Sep. 24, 2020

(65) Prior Publication Data
US 2022/0370362 A1    Nov. 24, 2022

(30) Foreign Application Priority Data

Mar. 15, 2019 (EP) ..................... 19163103

(51) Int. Cl.
*A61K 9/16* (2006.01)
*A61K 38/26* (2006.01)

(52) U.S. Cl.
CPC ............ *A61K 9/1688* (2013.01); *A61K 38/26* (2013.01)

(58) Field of Classification Search
CPC ......... A61K 9/1688; A61K 38/26; B01J 2/04; C07K 14/605
See application file for complete search history.

(56) References Cited

U.S. PATENT DOCUMENTS

| | | | |
|---|---|---|---|
| 6,187,704 B1 | 2/2001 | Takahashi et al. | |
| 6,560,897 B2 | 5/2003 | Chickering et al. | |
| 10,251,956 B2 | 4/2019 | Li et al. | |
| 10,933,120 B2 | 3/2021 | Vilhelmsen et al. | |
| 11,617,965 B2 | 4/2023 | Ingvarsson | |
| 2004/0223917 A1 | 11/2004 | Hindle et al. | |
| 2005/0031692 A1 | 2/2005 | Beyerinck et al. | |
| 2009/0226530 A1 | 9/2009 | Lassner et al. | |
| 2010/0183876 A1* | 7/2010 | Hell .................. | A61K 9/14 530/308 |
| 2016/0022582 A1 | 1/2016 | Alessi et al. | |
| 2016/0022620 A1 | 1/2016 | Suovaniemi | |
| 2016/0206562 A1 | 7/2016 | Kuwata | |
| 2018/0057558 A1* | 3/2018 | Penias Navon ...... | C07K 14/605 |

FOREIGN PATENT DOCUMENTS

| | | |
|---|---|---|
| CN | 101244111 A | 8/2008 |
| CN | 101400363 A | 4/2009 |
| CN | 101949635 A | 1/2011 |
| CN | 201926251 U | 8/2011 |
| CN | 105340883 A | 2/2016 |
| CN | 105517539 A | 4/2016 |
| CN | 106166396 A | 11/2016 |
| CN | 107812181 A | 3/2018 |
| CN | 207412769 U | 5/2018 |
| CN | 208287512 U | 12/2018 |
| EP | 2158029 A1 | 3/2010 |
| JP | 7410952 B2 | 1/2024 |
| RU | 2537139 C2 | 12/2014 |
| WO | 2001/093837 A2 | 12/2001 |
| WO | 2002036098 A1 | 5/2002 |
| WO | 02/098348 A2 | 12/2002 |
| WO | 2006097537 A2 | 9/2006 |
| WO | 2008051299 A2 | 5/2008 |
| WO | 2008/132224 A2 | 11/2008 |
| WO | 08133908 A2 | 11/2008 |
| WO | 2010072621 A2 | 7/2010 |
| WO | 2012112626 A2 | 8/2012 |
| WO | 2018069777 A1 | 4/2018 |
| WO | 2019038412 A1 | 2/2019 |

OTHER PUBLICATIONS

Contura (Benefits of a Cast Iron Stove, Nov. 8, 2018) (Year: 2018).*
European Standard EN 10088-1, Dec. 31, 2005 in 9 pages.
Worch, Operation Manual of B-290 Small Spray Dryer, Oct. 2005, pp. 1-14, 55-56.
Juliano et al., "Buccal tablets containing cysteine and chlorhexidine for the reduction of acetaldehyde levels in the oral cavity." Drug development and industrial pharmacy, Mar. 2011, vol. 37, No. 10, pp. 1192-1199.
Pakowski et al., "Drying of Pharmaceutical Products." pp. 689-712 IN Handbook of Industrial Drying, 2007, Edition 1, Chapter 29.
Shan et al., "Selective non-oxidative dehydrogenation of ethanol to acetaldehyde and hydrogen on highly dilute NiCu alloys." Applied Catalysis B: Environmental, Nov. 2017, vol. 205, pp. 541-550.

* cited by examiner

*Primary Examiner* — Lezah Roberts
*Assistant Examiner* — Abdulrahman Abbas
(74) *Attorney, Agent, or Firm* — Leon Y. Lum

(57) ABSTRACT

The present invention relates to a process for spray drying of a feed solution comprising semaglutide, said process comprising introducing the feed solution comprising semaglutide in a solvent into a spray dryer and introducing an atomising gas and a drying gas, characterised in that the spray dryer comprises a gas heater for the drying gas with an inner surface comprising iron and less than 18.5% chromium.

13 Claims, 1 Drawing Sheet

PROCESS FOR SPRAY DRYING A GLP-1 PEPTIDE

CROSS-REFERENCE TO RELATED APPLICATIONS

This application is a 35 U.S.C. § 371 National Stage application of International Application PCT/EP2020/056744 (WO/2020/187712), filed Mar. 13, 2020, which claims priority to European Patent Application 19163103.5, filed Mar. 15, 2019; the contents of which are incorporated herein by reference.

The present invention relates to the field of spray drying of a feed solution comprising a GLP-1 peptide, such as semaglutide. More specifically, the invention pertains to processes for spray drying of a feed solution comprising semaglutide wherein an improved purity is obtained, semaglutide obtainable by said process and its use in medicine.

BACKGROUND

Protein and peptide stability during processing and upon storage is of the utmost importance when manufacturing drug substances and drug products. During spray drying of drug substances, impurities may arise due to reactions between solvents and the drug substance. It is highly desirable to obtain processes for spray drying of drug substances, wherein as little impurities as possible are generated during the drying process and wherein the highest possible drug stability and drug purity are obtained.

It is known from the prior art that amino groups and certain amino acids can be used for binding of acetaldehydes and that acetaldehyde is capable of reacting with a variety of proteins to form both stable and unstable products. Unstable products are readily reversible, whereas stable products are essentially irreversible products that are characterized by their resistance to various treatments. It is furthermore known from the prior art that there exist instances of non-oxidative ethanol dehydrogenation to acetaldehyde catalysed by metal species.

SUMMARY

In some aspects the present invention relates to a process for spray drying of a feed solution comprising semaglutide, said process comprising introducing the feed solution comprising semaglutide in a solvent into a spray dryer and introducing an atomising gas and a drying gas, characterised in that the spray dryer comprises a gas heater for the drying gas with an inner surface comprising iron and less than 18.5% chromium.

In some aspects the present invention relates to a product obtainable by a process of the invention as well as uses of said product.

The present inventors have observed an increased amount of impurity generation upon moving a process for spray drying of a feed solution comprising semaglutide from a first unit to a second unit. The change in unit was facilitated by a need for increasing the production and both units are standard units for spray drying. The impurity was characterised as having an increased molar weight, corresponding to a product reacted with acetaldehyde. It was not apparent what the cause of impurities was but after extensive investigations and considerations it was evident that there was a significant correlation between the gas inlet temperature and the level of free acetaldehyde in the spray dried product, which then could react with the product. It furthermore appeared that the increased amount of impurity generation was caused by the gas heater material, since passing ethanol spiked nitrogen over material identical to the gas heater material showed ethanol dehydrogenation, dependent on the gas temperature. The present inventors have observed that a lower amount of impurities is generated when applying a gas heater made of stainless steel 316 in the spray drying process compared to when applying a gas heater made of Incoloy 800 in such processes. The present invention appears to be independent of production scale.

DESCRIPTION

Figure 1:
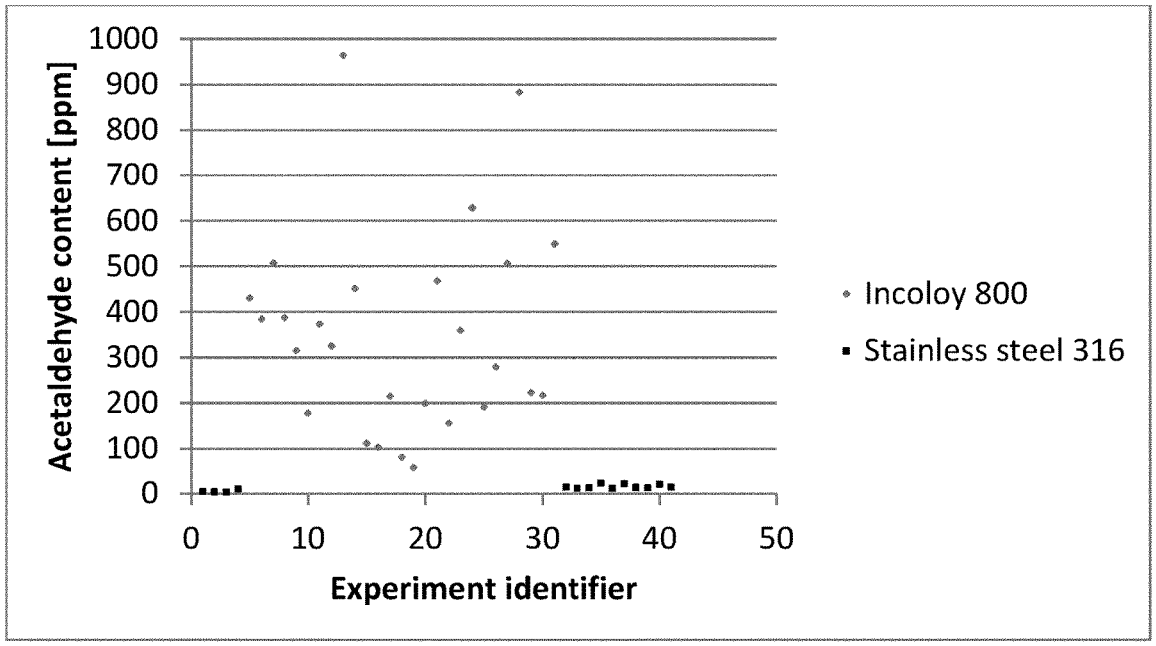
FIG. 1 shows acetaldehyde content (ppm) when using a gas heater made of Incoloy 800 or stainless steel 316 in the spray drying process.

In some embodiments the present invention relates to a process for spray drying of a feed solution comprising semaglutide, said process comprising introducing the feed solution comprising semaglutide in a solvent into a spray dryer and introducing an atomising gas and a drying gas, characterised in that the spray dryer comprises a gas heater for the drying gas with an inner surface comprising iron and less than 18.5% chromium.

In some embodiments the present invention relates to a product obtainable by a process of the invention as well as uses of said product.

Spray drying is often used as a step in the manufacture of drug substances and drug products. The purity of the obtained products is important for the overall product costs as well as the safety for subjects subsequently receiving the final drug product.

Gas Heater Material

Different material can be used for gas heaters. Different materials have different properties and are useful for different purposes.

Incoloy 800 is an iron-nickel-chromium alloy with moderate strength and good resistance to oxidation, carburization and sulfidation at elevated temperatures, such as above 800° C. It is particularly useful and widely used for high-temperature equipment, such as heat-treating equipment and heat exchangers in chemical processes. Incoloy 800 comprises iron, 30-35% nickel and 19-23% chromium along with other components (Special Metals Corporation, 2004 (September 4), publication number SMC-046).

Stainless steel is a term used to describe an extremely versatile family of materials with good corrosion and heat resistance. Stainless steel is generally considered to comprise iron and at least 10.5% chromium. Stainless steel 316 comprises iron, 16-18% chromium and 10-14% nickel along with other components (Specification Sheet: Alloy 316/316L (UNS S31600, S31603) W. Nr. 1.4401, 1.4404, Sandmeyer Steel Company 06/2014).

Process for Spray Drying

The present invention concerns a process for spray drying of a feed solution comprising a GLP-1 peptide. In one embodiment, the present invention concerns a process for spray drying of a feed solution comprising the GLP-1 peptide semaglutide, said process comprising a gas heater for drying gas with an inner surface comprising iron and less than 18.5% chromium. As used herein, the definition "inner surface" refers to the inside surface of the gas heater which is in contact with the drying gas. In some embodiments, the inner surface may have a depth of 0.001-50 cm, alternatively 0.01-30 cm, alternatively 0.1-10 cm. In some embodiments, the inner surface may have a depth of 0.001-0.1 cm, alternatively 0.001-0.5 cm, alternatively 0.001-1 cm, alternatively 0.001-2 cm, alternatively 0.001-3 cm, alternatively 0.001-4 cm, alternatively 0.001-5 cm, alternatively 0.001-6 cm, alternatively 0.001-7 cm, alternatively 0.001-8 cm, alternatively 0.001-9 cm, alternatively 0.001-10 cm. In some embodiments, the entire gas heater for drying gas comprises iron and less than 18.5% chromium.

In some embodiments of the present invention, the inner surface comprises 1-18.5% chromium, alternatively 5-18.5% chromium, alternatively 10-18.5% chromium, alternatively 14-18.5% chromium, alternatively 16-18% chromium. In some embodiments of the present invention, the inner surface comprises less than 29% nickel. In some embodiments, the inner surface comprises 1-29% nickel, alternatively 5-20% nickel, alternatively 6-18% nickel, alternatively 8-16% nickel, alternatively 10-14% nickel. In some embodiments of the present invention, the inner surface comprises 16-18% chromium and 10-14% nickel. In some embodiments of the present invention, the inner surface does not comprise aluminium. In some embodiments the inner surface does not comprise titanium.

In some embodiments of the present invention, the feed solution comprises a solution of a GLP-1 peptide in a solvent. In some embodiments of the present invention, the feed solution comprises a solution of GLP-1 peptide semaglutide in a solvent. In some embodiments of the present invention, the solvent is an aqueous alcoholic solvent such as aqueous ethanol, i.e. comprising water and ethanol. In some embodiments of the present invention, the feed solution consists substantially of semaglutide in aqueous ethanol. In some embodiments, the aqueous ethanol is in a concentration of 40-75% (w/w), alternatively 45-70% (w/w), alternatively 49-60% (w/w). The concentration of aqueous ethanol is defined from the content of ethanol, i.e. 70% (w/w) aqueous ethanol consists substantially of 70% ethanol and 30% water by weight. In some embodiments of the present invention, the concentration of semaglutide in the feed solution is 0.1-10% (w/w), alternatively 0.2-5% (w/w), alternatively 0.3-3% (w/w), alternatively 0.5-2.5% (w/w). In some embodiments of the present invention, the feed solution comprises 0.1-10% (w/w) semaglutide in 40-75% (w/w) aqueous ethanol. In some embodiments of the present invention, the feed solution comprises 0.5-2.5% (w/w) semaglutide in 49-60% (w/w) aqueous ethanol. In some embodiments of the present invention, the feed solution consists substantially of 0.5-2.5% (w/w) semaglutide in 49-60% (w/w) aqueous ethanol. As used herein, 'the feed solution consists substantially of semaglutide', refers to that other agents from the manufacturing process may be present, such as salts or peptide impurities; for example, the main component is semaglutide and no excipients have been added. In some embodiments of the present invention, the feed solution introduced into the spray dryer comes from a final chromatographic manufacturing step and will as a main solid component comprise semaglutide (80-100%), but also salts and impurities carried over from manufacture.

In some embodiments of the present invention, the drying gas is nitrogen. In some embodiments of the present invention, the drying gas is recirculated. In some embodiments of the present invention, the atomising gas is nitrogen. In some embodiments of the present invention, the atomising gas flow rate is 18-77 kg/h. In some embodiments of the present invention, the outlet temperature is 57-79° C. In some embodiments of the present invention, the inlet temperature is 100-162° C. In some embodiments of the present invention, the feed flow rate is 24-56 kg/h. In some embodiments of the present invention, the condenser temperature is between −5 to 5° C. In some embodiments of the present invention, the drying gas flow rate is 1250-1550 kg/h. In some embodiments of the present invention, the nozzle has an inside diameter of 1.0 mm and an outside diameter of 5-6.5 mm.

In some embodiments of the present invention, the process further comprises a step of formulating semaglutide obtained by the process into a pharmaceutical composition. In some embodiments, the pharmaceutical composition is a solid or liquid pharmaceutical composition. In some embodiments, the pharmaceutical composition is a tablet.

Semaglutide

The compound semaglutide may be prepared as described in WO2006/097537, Example 4. Semaglutide is also known as $N^{6,26}$-{18-[N-(17-carboxyheptadecanoyl)-L-γ-glutamyl]-10-oxo-3,6,12,15-tetraoxa-9,18-diazaoctadecanoyl}-[8-(2-amino-2-propanoic acid), 34-L-arginine]human glucagon-like peptide 1(7-37), see WHO Drug Information Vol. 24, No. 1, 2010.

In some embodiments, semaglutide may be present in its fully or partly ionised form; for example one or more carboxylic acid groups (—COOH) may be deprotonated into the carboxylate group (—COO$^-$) and/or one or more amino groups (—NH$_2$) may be protonated into the —NH$_3^+$ groups. In some embodiments, semaglutide is in the form of a salt.

Pharmaceutical Composition

The compound semaglutide may be administered in the form of a pharmaceutical composition. The pharmaceutical composition may comprise semaglutide in a concentration from 0.01 mg/ml to 100 mg/ml. In some embodiments the pharmaceutical composition comprises 0.01-50 mg/ml, or 0.01-20 mg/ml, or 0.01-10 mg/ml semaglutide. In some embodiments the pharmaceutical composition comprises 0.1-20 mg/ml semaglutide.

The pharmaceutical compositions described herein may further comprise one or more pharmaceutically acceptable excipients, for example selected from the group consisting of buffer system, preservative, tonicity agent, chelating agent, stabilizer and surfactant. In some embodiments the pharmaceutical composition comprises one or more pharmaceutically acceptable excipients, such as one or more selected from the group consisting of a buffer, an isotonic agent, and a preservative. The formulation of pharmaceutically active ingredients with various excipients is known in the art, see e.g. Remington: The Science and Practice of Pharmacy (e.g. 19th edition (1995), and any later editions). The term "excipient" broadly refers to any component other than the active therapeutic ingredient(s), e.g. compounds of the invention. The excipient may be an inert substance, an inactive substance, and/or a not medicinally active substance.

In some embodiments the pharmaceutical composition comprises a phosphate buffer, such as a sodium phosphate buffer, e.g. disodium phosphate. In some embodiments the pharmaceutical composition comprises an isotonic agent, such as propylene glycol. In some embodiments the pharmaceutical composition comprises a preservative, such as phenol.

The pharmaceutical composition may be in the form of a tablet. The pharmaceutical composition may comprise semaglutide in an amount from 0.01 mg to 100 mg. In some embodiments the pharmaceutical composition comprises 0.01-50 mg, alternatively 0.01-20 mg, alternatively 0.01-10 mg semaglutide. The pharmaceutical composition may be in the form of a solution or a suspension. The pharmaceutical composition may be suitable for sublingual and/or oral administration. The pharmaceutical composition may be suitable for subcutaneous administration Uses The product obtainable by the process of the invention is intended for use in a pharmaceutical composition together with one or more pharmaceutically acceptable excipients. In some embodiments, the product obtainable by the process of the invention is characterised by comprising less than 0.5%, alternatively 0.4%, alternatively 0.3%, alternatively 0.2% impurities. In some embodiments, the product obtainable by the process of the invention is for subcutaneous administration. In some embodiments, the product obtainable by the process is for sublingual and/or oral administration. In some embodiments, the pharmaceutical composition is in the form of a tablet.

In some embodiments, the product obtainable by the process of the invention is for use in medicine. In some embodiments the product obtainable by the process of the invention is for use in the prevention and/or treatment of obesity and/or diabetes. In some embodiments the product obtainable by the process of the invention is for use in the treatment of obesity. In some embodiments the product obtainable by the process of the invention is for use in the treatment of diabetes. In some embodiments the product obtainable by the process of the invention is for use in the prevention and/or treatment of overweight, obesity, hyperglycemia, type 2 diabetes, impaired glucose tolerance and/or type 1 diabetes. In some embodiments the product obtainable by the process of the invention is for use in the prevention and/or treatment of NASH.

In some embodiments the pharmaceutical composition is for use in the prevention and/or treatment of obesity and/or diabetes. In some embodiments the pharmaceutical composition is for use in the treatment of obesity and/or diabetes. In some embodiments the pharmaceutical composition is for use in the treatment of obesity. In some embodiments the pharmaceutical composition is for use in the treatment of diabetes. In some embodiments the pharmaceutical composition is for use in the prevention and/or treatment of overweight, obesity, hyperglycemia, type 2 diabetes, impaired glucose tolerance and/or type 1 diabetes. In some embodiments the pharmaceutical composition is for use in the prevention and/or treatment of NASH.

In some embodiments the present invention relates to a method of preventing and/or treating obesity and/or diabetes by administering to a subject in need thereof a therapeutically effective amount of the product obtainable by the process of the invention. In some embodiments the present invention relates to a method of treating obesity and/or diabetes by administering to a subject in need thereof a therapeutically effective amount of the product obtainable by the process of the invention. In some embodiments the present invention relates to a method of treating obesity by administering to a subject in need thereof a therapeutically effective amount of the product obtainable by the process of the invention. In some embodiments the present invention relates to a method of treating diabetes by administering to a subject in need thereof a therapeutically effective amount of the product obtainable by the process of the invention. In some embodiments the present invention relates to a method of preventing and/or treating overweight, obesity, hyperglycemia, type 2 diabetes, impaired glucose tolerance and/or type 1 diabetes by administering to a subject in need thereof a therapeutically effective amount of the product obtainable by the process of the invention. In some embodiments the present invention relates to a method of preventing and/or treating NASH by administering to a subject in need thereof a therapeutically effective amount of the product obtainable by the process of the invention.

In some embodiments the present invention relates to a method of preventing and/or treating obesity and/or diabetes by administering to a subject in need thereof a therapeutically effective amount of the pharmaceutical composition. In some embodiments the present invention relates to a method of treating obesity and/or diabetes by administering to a subject in need thereof a therapeutically effective amount of the pharmaceutical composition. In some embodiments the present invention relates to a method of treating obesity by administering to a subject in need thereof a therapeutically effective amount of the pharmaceutical composition. In some embodiments the present invention relates to a method of treating diabetes by administering to a subject in need thereof a therapeutically effective amount of the pharmaceutical composition. In some embodiments the present invention relates to a method of preventing and/or treating overweight, obesity, hyperglycemia, type 2 diabetes, impaired glucose tolerance and/or type 1 diabetes by administering to a subject in need thereof a therapeutically effective amount of the pharmaceutical composition. In some embodiments the present invention relates to a method of preventing and/or treating NASH by administering to a subject in need thereof a therapeutically effective amount of the pharmaceutical composition.

Unless otherwise stated, ranges herein include their end points. In some embodiments the term "a" means "one or more". In some embodiments, and unless otherwise indicated in the specification, terms presented in singular form also include the plural situation. Herein the term "about" means ±10% of the value referred to, and includes the value.

Non-Limiting Embodiments of the Invention

The following are non-limiting embodiments of the invention:
1. A process for spray drying of a feed solution comprising semaglutide, said process comprising introducing the feed solution comprising semaglutide in a solvent into a spray dryer and introducing an atomising gas and a drying gas, characterised in that the spray dryer comprises a gas heater for the drying gas with an inner surface comprising iron and less than 18.5% chromium.
2. The process according to embodiment 1, characterised in that the inner surface comprises 1-18.5% chromium.
3. The process according to any one of the preceding embodiments, characterised in that the inner surface comprises 5-18.5% chromium.

4. The process according to any one of the preceding embodiments, characterised in that the inner surface comprises 10-18.5% chromium.
5. The process according to any one of the preceding embodiments, characterised in that the inner surface comprises 14-18.5% chromium.
6. The process according to any one of the preceding embodiments, characterised in that the inner surface comprises 16-18% chromium.
7. The process according to any one of the preceding embodiments, characterised in that the inner surface comprises less than 29% nickel.
8. The process according to any of the preceding embodiments, characterised in that the inner surface comprises 1-29% nickel.
9. The process according to any of the preceding embodiments, characterised in that the inner surface comprises 5-20% nickel.
10. The process according to any of the preceding embodiments, characterised in that the inner surface comprises 6-18% nickel.
11. The process according to any of the preceding embodiments, characterised in that the inner surface comprises 8-16% nickel.
12. The process according to any of the preceding embodiments, characterised in that the inner surface comprises 10-14% nickel.
13. The process according to any of the preceding embodiments, characterised in that the inner surface comprises 16-18% chromium and 10-14% nickel.
14. The process according to any one of the preceding embodiments, characterised in that the inner surface does not comprise aluminium.
15. The process according to any one of the preceding embodiments, characterised in that the inner surface does not comprise titanium.
16. The process according to any one of the preceding embodiments, characterised in that the inner surface has a depth of 0.001-10 cm.
17. The process according to any one of the preceding embodiments, characterised in that the entire gas heater for the drying gas comprises iron and less than 18.5% chromium.
18. The process according to any one of the preceding embodiments, characterised in that the feed solution consists substantially of semaglutide in a solvent.
19. The process according to any one of the preceding embodiments, characterised in that the feed solution solvent comprises an organic alcoholic solvent.
20. The process according to any one of the preceding embodiments, characterised in that the feed solution solvent comprises ethanol.
21. The process according to any one of the preceding embodiments, characterised in that the feed solution comprises aqueous ethanol.
22. The process according to any one of the preceding embodiments, characterised in that the feed solution solvent is 40-75% (w/w) aqueous ethanol.
23. The process according to any one of the preceding embodiments, characterised in that the feed solution solvent is 45-70% (w/w) aqueous ethanol.
24. The process according to any one of the preceding embodiments, characterised in that the feed solution solvent is 49-60% (w/w) aqueous ethanol.
25. The process according to any one of the preceding embodiments, characterised in that the feed solution comprises 0.1-10% (w/w) semaglutide.
26. The process according to any one of the preceding embodiments, characterised in that the feed solution comprises 0.2-5% (w/w) semaglutide.
27. The process according to any one of the preceding embodiments, characterised in that the feed solution comprises 0.3-3% (w/w) semaglutide.
28. The process according to any one of the preceding embodiments, characterised in that the feed solution comprises 0.5-2.5% (w/w) semaglutide.
29. The process according to any one of the preceding embodiments, characterised in that the feed solution comprises 0.1-10% (w/w) semaglutide in 40-75% (w/w) aqueous ethanol.
30. The process according to any one of the preceding embodiments, characterised in that the feed solution comprises 0.5-2.5% (w/w) semaglutide in 49-60% (w/w) aqueous ethanol.
31. The process according to any one of the preceding embodiments, characterised in that the feed solution consists substantially of 0.5-2.5% (w/w) semaglutide in 49-60% (w/w) aqueous ethanol.
32. The process according to any one of the preceding embodiments, characterised in that the drying gas is nitrogen.
33. The process according to any one of the preceding embodiments, characterised in that the drying gas is recirculated.
34. The process according to any one of the preceding embodiments, characterised in that the atomising gas is nitrogen.
35. The process according to any one of the preceding embodiments, characterised in having an atomising gas flow rate of 18-77 kg/h.
36. The process according to any one of the preceding embodiments, characterised in having an outlet temperature of 57-79° C.
37. The process according to any one of the preceding embodiments, characterised in having an inlet temperature of 100-162° C.
38. The process according to any one of the preceding embodiments, characterised in having a feed flow rate of 24-56 kg/h.
39. The process according to any one of the preceding embodiments, characterised in having a condenser temperature between −5 to 5° C.
40. The process according to any one of the preceding embodiments, characterised in having a drying gas flow rate of 1250-1550 kg/h.
41. The process according to any one of the preceding embodiments characterised in having a nozzle with an inside diameter of 1.0 mm and an outside diameter of 5-6.5 mm.
42. The process according to any one of the preceding embodiments further comprising a step of formulating semaglutide obtained by said process into a pharmaceutical composition.
43. The process according to embodiment 42, wherein said pharmaceutical composition is a solid or liquid pharmaceutical composition.
44. The process according to embodiment 42, wherein said pharmaceutical composition is a tablet.
45. The product obtainable by the process according to any one of the preceding embodiments.
46. The product according to embodiment 45 characterised by comprising less than 0.5%, alternatively 0.4%, alternatively 0.3%, alternatively 0.2% impurities.

47. A pharmaceutical composition comprising a therapeutically effective amount of the product according to any one of embodiments 45-46.
48. The pharmaceutical composition according to embodiment 47 further comprising one or more pharmaceutically acceptable excipients.
49. The pharmaceutical composition according to any one of embodiments 47-48 suitable for sublingual and/or oral administration.
50. The pharmaceutical composition according to any one of embodiments 47-49 suitable for subcutaneous administration.
51. The pharmaceutical composition according to any one of embodiments 47-50 in the form of a tablet.
52. The product according to any one of embodiments 45-46 or the pharmaceutical composition according to any one of embodiments 47-51 for use in medicine.
53. The product according to any one of embodiments 45-46 or the pharmaceutical composition according to any one of embodiments 47-51 for use in the prevention and/or treatment of obesity and/or diabetes.
54. The product according to any one of embodiments 45-46 or the pharmaceutical composition according to any one of embodiments 47-51 for use in the treatment of obesity and/or diabetes.
55. The product according to any one of embodiments 45-46 or the pharmaceutical composition according to any one of embodiments 47-51 for use in the treatment of obesity.
56. The product according to any one of embodiments 45-46 or the pharmaceutical composition according to any one of embodiments 47-51 for use in the treatment of diabetes.
57. The product according to any one of embodiments 45-46 or the pharmaceutical composition according to any one of embodiments 47-51 for use in the prevention and/or treatment of overweight, obesity, hyperglycemia, type 2 diabetes, impaired glucose tolerance and/or type 1 diabetes.
58. The product according to any one of embodiments 45-46 or the pharmaceutical composition according to any one of embodiments 47-51 for use in the prevention and/or treatment of NASH.
59. A method of preventing and/or treating obesity and/or diabetes by administering to a subject in need thereof a therapeutically effective amount of the product obtainable by the process of any one of embodiments 1-44, the product according to any one of embodiments 45-46 or the pharmaceutical composition according to any one of embodiments 47-51.
60. A method of treating obesity and/or diabetes by administering to a subject in need thereof a therapeutically effective amount of the product obtainable by the process of any one of embodiments 1-44, the product according to any one of embodiments 45-46 or the pharmaceutical composition according to any one of embodiments 47-51.
61. A method of treating obesity by administering to a subject in need thereof a therapeutically effective amount of the product obtainable by the process of any one of embodiments 1-44, the product according to any one of embodiments 45-46 or the pharmaceutical composition according to any one of embodiments 47-51.
62. A method of treating diabetes by administering to a subject in need thereof a therapeutically effective amount of the product obtainable by the process of any one of embodiments 1-44, the product according to any one of embodiments 45-46 or the pharmaceutical composition according to any one of embodiments 47-51.
63. A method of preventing and/or treating overweight, obesity, hyperglycemia, type 2 diabetes, impaired glucose tolerance and/or type 1 diabetes by administering to a subject in need thereof a therapeutically effective amount of the product obtainable by the process of any one of embodiments 1-44, the product according to any one of embodiments 45-46 or the pharmaceutical composition according to any one of embodiments 47-51.
64. A method of preventing and/or treating NASH by administering to a subject in need thereof a therapeutically effective amount of the product obtainable by the process of any one of embodiments 1-44, the product according to any one of embodiments 45-46 or the pharmaceutical composition according to any one of embodiments 47-51.

EXAMPLES

General Methods

Spray drying experiments were carried out on PSD4 manufacturing scale spray dryers using a two-fluid nozzle with an inner diameter of 1 mm and an outer diameter of 5-6.5 mm. Atomising gas was nitrogen and drying gas was nitrogen. The drying gas was recirculated via a condensing unit at −5 to 5° C. and then heated using gas heaters with an inner surface made of either Incoloy 800 or stainless steel 316.

Feed Solution Preparation:

Feed solution was either 1) received as semaglutide in a water/ethanol solution from the previous manufacturing step or; 2) spray dried powder comprising semaglutide, re-dissolved in the appropriate water/ethanol composition before processing. Semaglutide concentration tested was in the range of 7.8 to 24 g/l and ethanol weight percentage of the solvent system was in the range of 49-60% when tested.

Spray Drying Process:

Solvent used for stabilisation matched the water/ethanol composition of the solution containing semaglutide (49-60% (w/w) ethanol).

Before batch initiation the spray dryer was stabilised with solvent on the required set point values (pre-defined from Table 1 below) for drying gas flow, outlet temperature, feed flow, atomising gas flow and condenser temperature and the inlet temperature adjusted to obtain the required outlet temperature.

TABLE 1

Lower and upper limits of the parameters tested in the spray drying process.

| Parameters | Lower limit tested | Upper limit tested |
| --- | --- | --- |
| Outlet temperature [° C.] | 57 | 79 |
| Atomising gas flow rate [kg/h] | 18 | 77 |
| Feed flow rate [kg/h] | 24 | 56 |
| Inlet temperature [° C.] | 100 | 162 |
| Condenser temperature | −5 | 5 |
| Drying gas flow [kg/h] | 1250 | 1550 |
| Semaglutide concentration [mg/ml] | 7.8 | 24.0 |
| Ethanol concentration in solvent [%] | 49 | 60 |

Once stable parameters were achieved, a switch was made from stabilisation solvent to the semaglutide feed solution to initiate the spray drying process. Product was collected using filter bag sleeves with filter bag blowback at pre-defined intervals or using cyclone as the main powder separation technique. At the end of the spray drying run, a switch from semaglutide feed solution to stabilisation solvent was made, before the unit was shut down, or stabilised for the following batch.

Example 1: Spray Drying Semaglutide Using Different Heater Material

Purpose: The purpose of this experiment was to identify the cause of impurity generation and means for preventing impurity generation.

Figure 2:
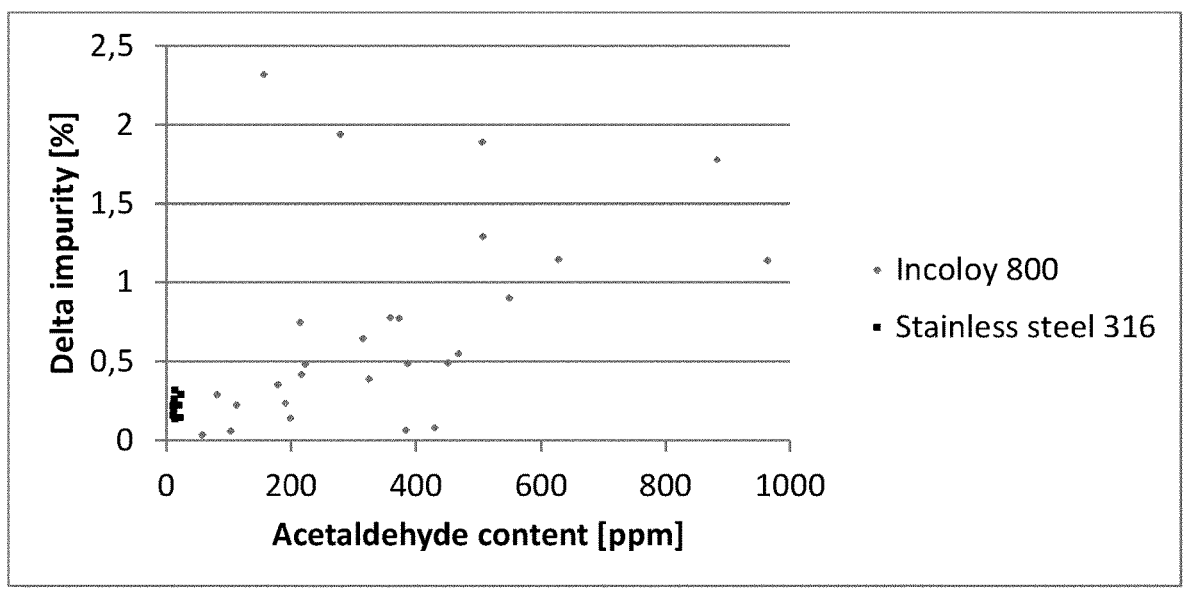
FIG. 2 shows the amount of impurities (%) generated during spray drying as function of acetaldehyde content (ppm) when using a gas heater made of Incoloy 800 or stainless steel 316 in the spray drying process.

Data Analysis:

The data presented in Table 2, FIG. 1 and FIG. 2 were analysed using standard least squares analysis using the SAS JMP® software version 12.2. Modelling the levels of acetaldehyde in the spray dried powder as a response it was positively influenced by the gas heater material and the inlet temperature and negatively influenced by the feed flow. Modelling the impurity increase as a response it was positively influenced by both the acetaldehyde level in the spray dried powder as well as the inlet temperature, although the inter-correlation between the two parameters is not deconvoluted.

TABLE 2

Acetaldehyde and impurity levels in response to different gas heater material

| Experiment identifier | Gas heater type | acetaldehyde (Hg/g) | delta HC1 [%] |
|---|---|---|---|
| 1 | Stainless steel 316 | 4.1 | |
| 2 | Stainless steel 316 | 3.7 | |
| 3 | Stainless steel 316 | 3 | |
| 4 | Stainless steel 316 | 10 | |
| 5 | Incoloy 800 | 430 | 0.0804 |
| 6 | Incoloy 800 | 384 | 0.0653 |
| 7 | Incoloy 800 | 507 | 1.2887 |
| 8 | Incoloy 800 | 387 | 0.4874 |
| 9 | Incoloy 800 | 315 | 0.6456 |
| 10 | Incoloy 800 | 178 | 0.3543 |
| 11 | Incoloy 800 | 81.1 | 0.2904 |
| 12 | Incoloy 800 | 57.2 | 0.0366 |
| 13 | Incoloy 800 | 103 | 0.0608 |
| 14 | Incoloy 800 | 215 | 0.7465 |
| 15 | Incoloy 800 | 325 | 0.3894 |
| 16 | Incoloy 800 | 373 | 0.7717 |
| 17 | Incoloy 800 | 199 | 0.1424 |
| 18 | Incoloy 800 | 964 | 1.1378 |
| 19 | Incoloy 800 | 451 | 0.4908 |
| 20 | Incoloy 800 | 112 | 0.2246 |
| 21 | Incoloy 800 | 279 | 1.9411 |
| 22 | Incoloy 800 | 217 | 0.4173 |
| 23 | Incoloy 800 | 506 | 1.8929 |
| 24 | Incoloy 800 | 883 | 1.7807 |
| 25 | Incoloy 800 | 223 | 0.483 |
| 26 | Incoloy 800 | 156 | 2.3196 |
| 27 | Incoloy 800 | 468 | 0.5491 |
| 28 | Incoloy 800 | 359 | 0.7769 |
| 29 | Incoloy 800 | 628 | 1.144 |
| 30 | Incoloy 800 | 191 | 0.2369 |
| 31 | Incoloy 800 | 549 | 0.9006 |
| 32 | Stainless steel 316 | 14 | 0.1366 |
| 33 | Stainless steel 316 | 11 | 0.1595 |
| 34 | Stainless steel 316 | 12 | 0.1952 |
| 35 | Stainless steel 316 | 23 | 0.2915 |
| 36 | Stainless steel 316 | 11 | 0.2171 |
| 37 | Stainless steel 316 | 22 | 0.1438 |
| 38 | Stainless steel 316 | 13 | 0.261 |
| 39 | Stainless steel 316 | 12 | 0.2277 |
| 40 | Stainless steel 316 | 20 | 0.2238 |
| 41 | Stainless steel 316 | 14 | 0.3171 |

The results in Table 2 and FIG. 1 show that conducting the spray drying process in a first unit comprising a gas heater made of stainless steel 316 generates low amounts of acetaldehyde. When conducting the spray drying process in a second unit comprising a gas heater made of Incoloy 800 increased amounts of acetaldehyde are generated. When replacing the Incoloy 800 gas heater material in the second unit with stainless steel 316 low amounts of acetaldehyde are generated. This shows that applying a gas heater made of stainless steel 316 in the spray drying process generates decreased amounts of acetaldehyde as compared to applying a gas heater made of Incoloy 800.

The results in Table 2 and FIG. 2 show that no impurity levels were measured for the first unit, as no problem had yet been identified. When conducting the spray drying process in a second unit comprising a gas heater made of Incoloy 800 high amounts of impurities were generated. When replacing the Incoloy 800 gas heater material in the second unit with stainless steel 316 low amounts of impurities were generated. This shows that applying a gas heater made of stainless steel 316 in the spray drying process generates decreased amounts of impurities as compared to applying a gas heater made of Incoloy 800. FIG. 2 furthermore shows the correlation between generated acetaldehyde and generated impurities.

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

The invention claimed is:

1. A process for spray drying a feed solution, comprising introducing the feed solution into a spray dryer and introducing an atomising gas and a drying gas into the spray dryer, wherein the feed solution comprises semaglutide, and wherein the spray dryer comprises a gas heater with an inner surface comprising (i) iron and 16-18% chromium or (ii) iron, chromium, and 10-14% nickel.

2. The process according to claim 1, wherein the inner surface comprises 16-18% chromium and 10-14% nickel.

3. The process according to claim 1, wherein the inner surface has a depth of 0.001 cm to 10 cm.

4. The process according to claim 1, wherein the feed solution solvent further comprises ethanol.

5. The process according to claim 1, wherein the feed solution comprises 0.5-2.5% (w/w) semaglutide in 49-60% (w/w) aqueous ethanol.

6. The process according to claim 1, wherein the drying gas is nitrogen.

7. The process according to claim 1, further comprising recirculating the drying gas.

8. A pharmaceutical composition obtained by the process according to claim 1.

9. The pharmaceutical composition according to claim 8, wherein the composition comprises less than 0.3% impurities.

10. The process according to claim 1, wherein the inner surface comprises 16-18% chromium and 10-14% nickel, wherein the feed solution comprises 0.5-2.5% (w/w) semaglutide in 49-60% (w/w) aqueous ethanol.

11. The process according to claim 10, wherein the drying gas is nitrogen.

12. The process according to claim 10, further comprising recirculating the drying gas.

13. The process according to claim 12, wherein the drying gas is nitrogen.

\* \* \* \* \*

UNITED STATES PATENT AND TRADEMARK OFFICE
CERTIFICATE OF CORRECTION

PATENT NO. : 12,138,349 B2
APPLICATION NO. : 17/438969
DATED : November 12, 2024
INVENTOR(S) : Ole Vangsgaard et al.

Page 1 of 1

It is certified that error appears in the above-identified patent and that said Letters Patent is hereby corrected as shown below:

In the Claims

At Column 12, Claim number 4, Line number 47, replace as follows "solution further comprises ethanol".

Signed and Sealed this
Tenth Day of June, 2025

Coke Morgan Stewart
*Acting Director of the United States Patent and Trademark Office*